US006176135B1

(12) United States Patent
Dubois et al.

(10) Patent No.: US 6,176,135 B1
(45) Date of Patent: Jan. 23, 2001

(54) SYSTEM AND METHOD FOR LASER-ULTRASONIC FREQUENCY CONTROL USING OPTIMAL WAVELENGTH TUNING

(76) Inventors: Marc Dubois, 40 Stoney Creek Dr., Clifton Park, NY (US) 12065; Peter W. Lorraine, 876 Heather La., Niskayuna, NY (US) 12309; Barbara Venchiarutti, 1306 Union St., Schenectady, NY (US) 12308; Robert J. Filkins, 122 Pilling Dr., Fonda, NY (US) 12068; Anthony S. Bauco, 32 Velina Dr., Burnt Hills, NY (US) 12027

(*) Notice: Under 35 U.S.C. 154(b), the term of this patent shall be extended for 0 days.

(21) Appl. No.: 09/361,768
(22) Filed: Jul. 27, 1999
(51) Int. Cl.[7] .................................................. G01N 29/04
(52) U.S. Cl. .............................. 73/643; 702/40; 372/28
(58) Field of Search .................. 73/643; 702/40; 372/9, 26, 28

(56) References Cited
U.S. PATENT DOCUMENTS 4,633,715 * 1/1987 Monchalin .............................. 73/657
4,683,750 * 8/1987 Kino et al. ............................. 73/606
5,814,730 * 9/1998 Brodeur et al. ........................ 73/597
5,982,482 * 11/1999 Nelson et al. ...................... 356/237.1

* cited by examiner

*Primary Examiner*—Richard A. Moller
(74) *Attorney, Agent, or Firm*—Gray Cary Ware and Freidenrich, LLP

(57) ABSTRACT

A system and method for generating a desired acoustic frequency content in a laser-generated ultrasonic wave emitted from a target in response to a laser pulse. The method includes generating a generation laser pulse using a laser source. An optimal wavelength $\lambda_0$ for the generation laser pulse is determined using a computer. The optimal wavelength data is determined from material-specific, empirically calculated data stored in a storage device that is accessible to the computer. An optimal laser pulse is generated by shifting the generation laser pulse to the optimal wavelength $\lambda_0$. The optimal laser pulse is directed to the target to generate the laser-generated ultrasonic wave with the desired frequency content.

31 Claims, 3 Drawing Sheets

SYSTEM AND METHOD FOR LASER-ULTRASONIC FREQUENCY CONTROL USING OPTIMAL WAVELENGTH TUNING

TECHNICAL FIELD OF THE INVENTION

This invention relates generally to the field of ultrasonic laser testing, and more particularly a method and system for optimizing the frequency content of laser-generated ultrasonic waves for target inspection.

BACKGROUND OF THE INVENTION

The use of advanced composite structures has experienced tremendous growth in the aerospace, automotive and other commercial industries. Non-destructive evaluation (NDE) methods are often employed to detect inclusions, delaminations and porosities in an effort to ascertain the structural integrity of the composite structures. One method of NDE is laser ultrasound.

Laser ultrasound involves the use of lasers for generation and detection of ultrasound in materials such as composites. The technique offers the potential of rapid, non-contact inspection. Typically, a laser source produces ultrasonic surface displacements on the surface of a remote target. A second probe laser beam can detect the ultrasonic surface displacement on the surface of the remote target. Collection optics and instrumentation can then be used to process the probe laser beam and output data representing the ultrasonic surface displacements on the surface of the target.

FIG. 1 illustrates a conventional laser ultrasound inspection method. FIG. 1 employs pulse laser 10 to inspect an object, such as aircraft 16. Pulse laser 10 emits generation pulse 12 which is directed towards scanning mirror 14. Scanning mirror 14 steers generation pulse 12 to inspect aircraft 16. Various lenses for focusing may also be employed. A $CO_2$ pulse laser may be employed as pulse laser 10. Pulse laser 10 deposits generation pulse 12 over a certain depth in an area on aircraft 16. Generation pulse 12 is converted to heat and causes expansion of an inspected area on aircraft 16. The expansion of the inspected area on aircraft 16 generates laser-generated ultrasonic waves.

The frequency content of the laser-generated ultrasonic waves contributes to the success of laser ultrasound as an NDE method. Higher frequencies yield better spatial resolution. However, for certain materials such as composites, high frequencies are attenuated more rapidly than lower frequencies. The thicker and more attenuative the component to be inspected, the lower the ultrasonic frequency content must be to avoid large attenuation. Consequently, with conventional methods the resolution and accuracy of defect detection tends to be limited for more attenuative materials.

SUMMARY OF THE INVENTION

In light of the above, a need exists for a system and method that generates a desired frequency content in laser-generated ultrasonic waves used for NDE. The present invention provides a system and method for ultrasonic laser inspection that substantially eliminates or reduces disadvantages and problems associated with previously developed systems and methods for ultrasonic laser inspection.

More specifically, the present invention provides a method for generating a desired acoustic frequency content in a laser-generated ultrasonic wave emitted from a remote target in response to a generation laser pulse. The method includes generating the generation laser pulse using a laser source. An optimal wavelength $\lambda_0$ for the laser pulse is determined using a computer. The optimal wavelength $\lambda_0$ is determined from material-specific, empirically calculated data stored in a storage device that is accessible to the computer. An optimal laser pulse is generated by shifting the generation laser pulse to the optimal wavelength $\lambda_0$. The optimal laser pulse is directed to the remote target to generate the laser-generated ultrasonic wave with the desired frequency content.

The present invention provides an important technical advantage in that a laser-generated ultrasonic wave can be generated with a desired frequency content. Thus, for certain materials that require a specific range for frequencies to adequately inspect the material, an optimal optical penetration depth $\mu_0$ can be determined. Based on the necessary optimal optical penetration depth $\mu_0$, an optimal wavelength $\lambda_0$ for the optimal laser pulse can be determined. In turn, the optimal wavelength S0 to generate the optimal laser pulse wavelength that products the desired range of frequencies in the laser-generated ultrasonic wave is obtained by tuning the source laser wavelength or by shifting the generation pulse laser wavelength using a shifting device such as an optical parametric oscillator. Therefore, depending on the thickness of the material or material composition, the desired frequencies can be generated to produce the best resolution for inspection. Additionally, the attenuation of the ultrasound can be controlled allowing a user to optimize their inspection techniques for the defects to be searched for. Furthermore, by understanding the attenuation characteristics of the ultrasound generated in the target, the scanning technique can be optimized based on these characteristics to reduce or eliminate over sampling and therefore increase the speed and efficiency of the inspection.

BRIEF DESCRIPTION OF THE DRAWINGS

A more complete understanding of the present invention and the advantages thereof may be acquired by referring to the following description, taken in conjunction with the accompanying drawings in which like reference numbers indicate like features and wherein.

DETAILED DESCRIPTION OF THE INVENTION

Preferred embodiments of the present invention are illustrated in the FIGUREs, like numerals being used to refer to like and corresponding parts of various drawings.

Figure 1:
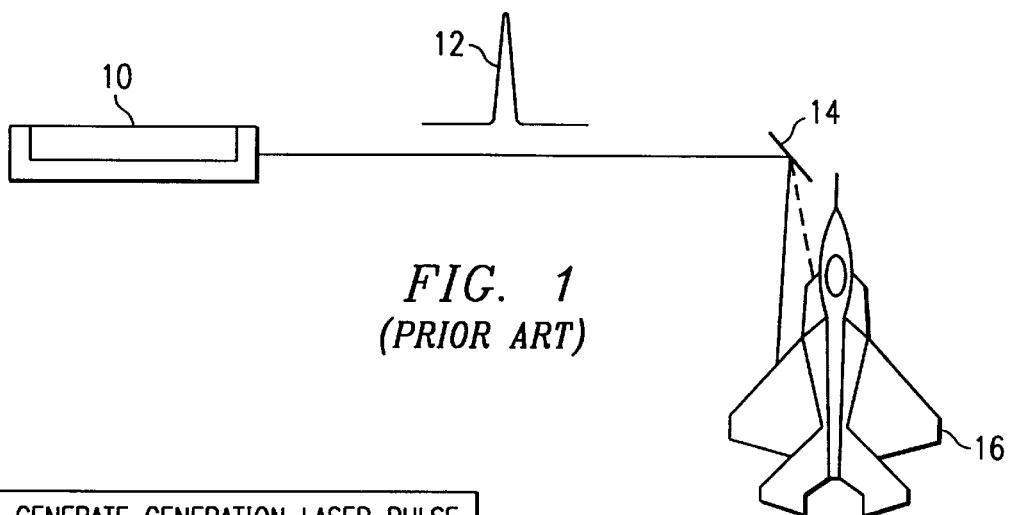
FIG. 1 illustrates a conventional laser ultrasound inspection method.
Figure 2:
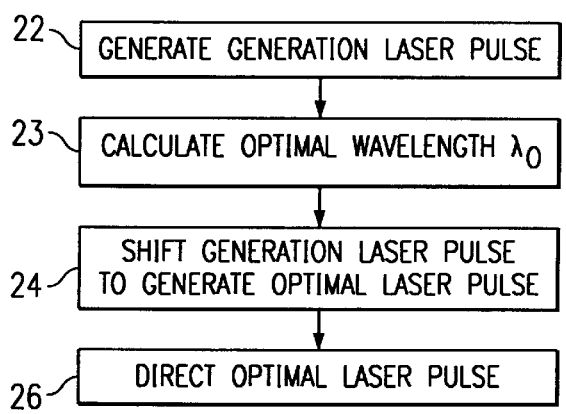
FIG. 2 is a flow diagram of one embodiment of the present invention.

The present invention provides a system and method for laser-ultrasonic frequency control using optimal wavelength tuning. FIG. 2 is a flow diagram illustrating one embodiment of the present invention. At step 22, an optimal wavelength $\lambda_0$ for the generation laser pulse is determined using a computer. At step 23, a generation laser pulse is generated using a laser source. The optimal wavelength data can be determined from material-specific, empirically calculated data stored in a storage device in or accessible to the computer. At step 24, an optimal laser pulse is generated by shifting the generation laser pulse to the optimal wavelength $\lambda_0$.

The generation laser pulse is generated from a laser source which may include neodynium laser, erbium laser, holmium laser, thulium laser, excimer laser, chromium laser, fosterite laser, alexandrite laser, dye laser, titanium sapphire laser, diode laser, limp pumped laser or other laser known to those skilled in the art. The material specific data values may vary for different materials such as various composites, as well as for different thicknesses of materials. At step 26, the optimal laser pulse can be directed toward the target.

Figure 3:
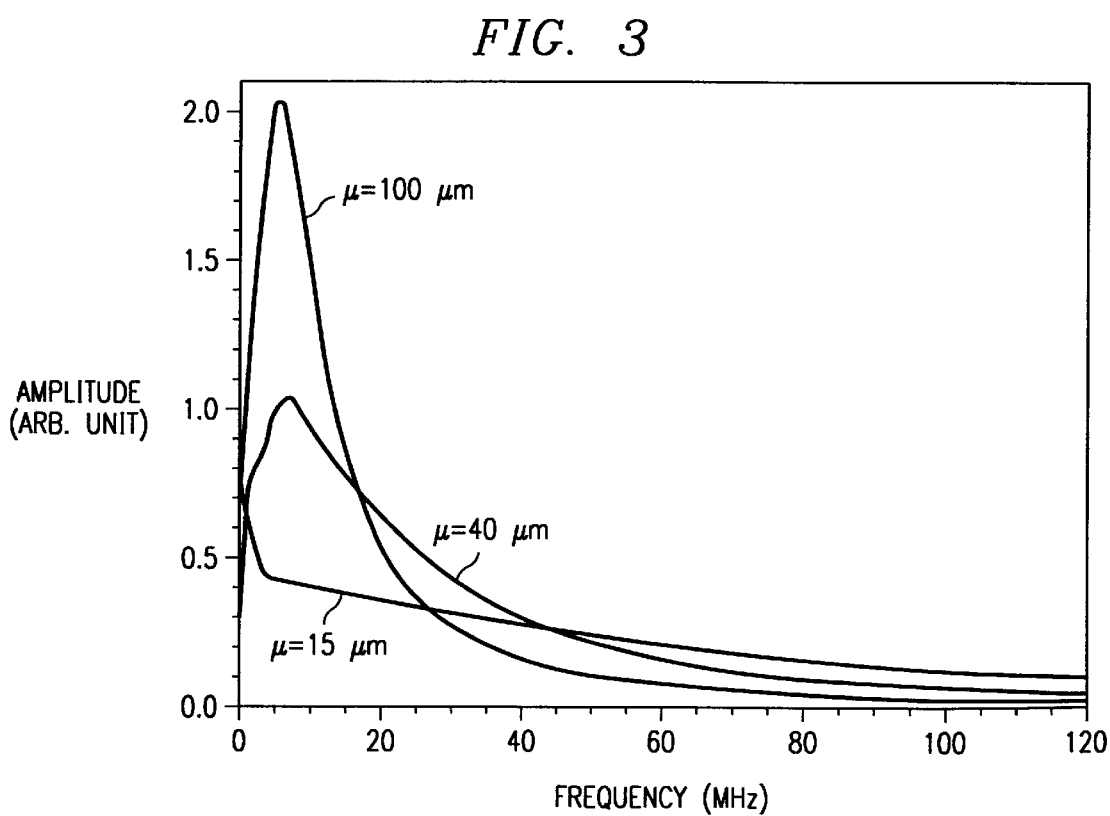
FIG. 3 represents the frequency spectra of the first back wall echoes and a reflection configuration calculated using a sophisticated model for a graphite-epoxy composite.
Figure 4:
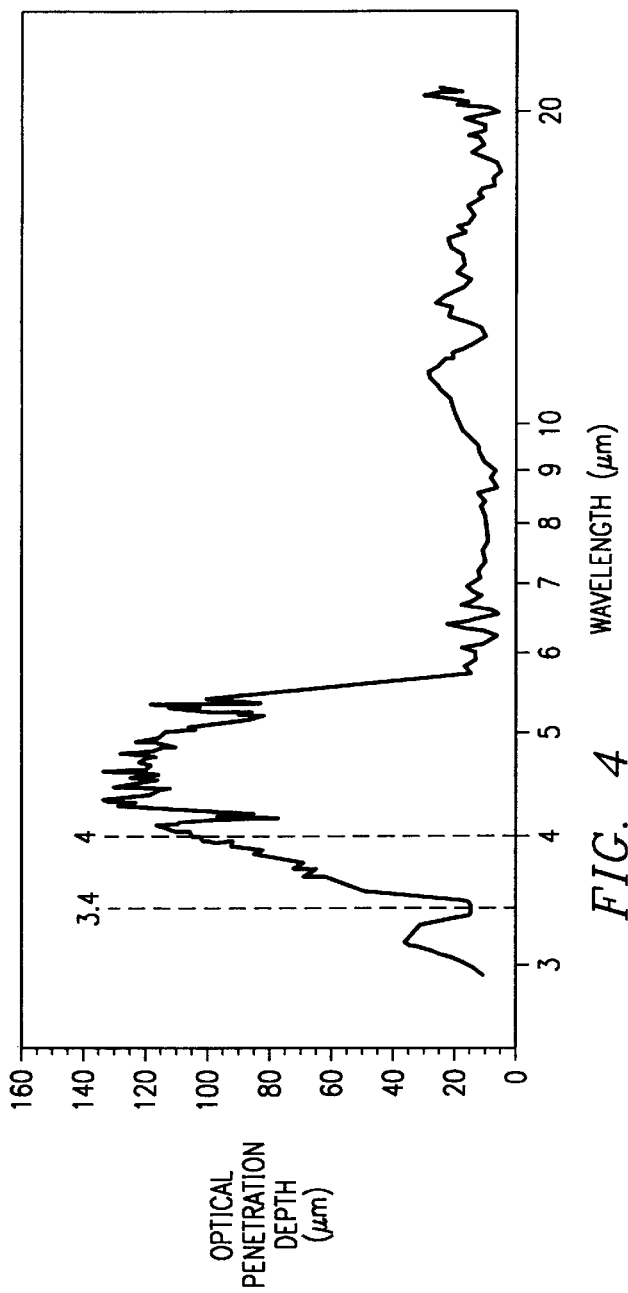
FIG. 4 represents experimental photo-acoustic spectroscopy data showing optical penetration depth l in an epoxy used as a matrix in graphite-epoxy composites.

The following discussion in reference to FIGS. 3 and 4 is presented to provide the basis for understanding the type of data that can be stored in the storage device and how the data can be used to determine the optimal wavelength $\lambda_0$. The optimal wavelength $\lambda_0$ is the wavelength of the optimal laser pulse necessary to generate the desired frequency content in the laser-generated ultrasonic wave.

The frequency content of the laser-generated ultrasonic waves is dictated by a combination of the optical penetration depth $\mu$ at the generation laser optical wavelength $\lambda$ and the temporal profile of the generation laser pulse. If the ultrasonic propagation delay of the laser-generated ultrasonic wave inside the optical penetration depth $\mu$ is much shorter than the generation laser pulse duration, the frequency content of the laser-generated ultrasonic waves is directly related to the duration of the generation laser pulse. On the other hand, if the generation laser pulse duration is much shorter than the ultrasonic propagation delay inside the optical penetration depth $\mu$, the frequency content is directly related to optical penetration depth $\mu$. In the latter case, by controlling the optical penetration depth $\mu$, the frequency content of the laser-generated ultrasonic wave may also be controlled.

FIG. 3 represents the frequency spectra of the first back wall echoes in a reflection configuration calculated using the sophisticated model for a graphite-epoxy composite with optical penetration depth $\mu$ of 100 $\mu$m, 40 $\mu$m, and 15 $\mu$m. Along the y-axis is the amplitude of the back wall echoes, while along the x-axis is the frequency of the back wall echoes. In the cases presented in FIG. 3, if the ultrasonic frequency of 80 MHz is used, the wavelength $\mu_{15}$ corresponding to a optical penetration depth $\mu$=15 $\mu$m is approximately two times more efficient than the wavelength $\lambda_{40}$ corresponding to the optical penetration depth $\mu$=40 $\mu$m and four times more efficient than the wavelength $\lambda_{100}$ corresponding to the optical penetration depth $\mu$=100 $\mu$m. However, if the ultrasonic frequency of 10 MHz is required, the wavelength $\lambda_{100}$ corresponding to an optical penetration depth $\mu$=100 $\mu$m is approximately two times more efficient than the wavelength $\lambda_{40}$ corresponding to the optical penetration depth $\mu$=40 $\mu$m and four times more efficient than the wavelength $\lambda_{15}$ corresponding to the optical penetration depth $\mu$=15 $\mu$m. In an intermediate case, a wavelength $\lambda$ corresponding to an optical penetration depth between 15 $\mu$m and 100 $\mu$m would be the most efficient wavelength.

In the frequency spectrum presented in FIG. 3, if the desired frequency content of the laser-generated ultrasonic waves must be higher than 40 MHz, the optimal wavelength $\lambda_0$ corresponding to an optimal optical penetration depth $\mu_0$ of 15 $\mu$m should be chosen. For an ultrasonic frequency content between 20 and 40 MHz, an optimal wavelength $\lambda_0$ corresponding to an optimal an optical penetration depth $\mu_0$ around 40 $\mu$m is appropriate. Finally, for an ultrasonic frequency content below 20 MHz, the optimal wavelength $\lambda_0$ corresponding to an optimal optical penetration depth $\mu_0$ of 100 $\mu$m should be chosen.

FIG. 4 represents experimental photo-acoustic spectroscopy data showing optical penetration depth 1 in an epoxy used as a matrix in graphite-epoxy composites. Along the y-axis is the optical penetration depth $\mu$ and along the x-axis is the wavelength $\lambda$ of the laser pulse needed to achieve the corresponding optical penetration depth $\mu$. The dotted lines indicate the range of operation for a laser generation system with tunable wavelength. At 3.4 $\mu$m wavelength the optical penetration depth $\mu$=15 $\mu$m, and at 4 $\mu$m wavelength $\lambda$, the optical penetration depth $\mu$>100 $\mu$m. Therefore, FIG. 2 illustrates that a system capable of tuning the generation laser wavelength between 3.4 and 4 micrometers has access to optical penetration depth between 15 $\mu$m and 100 $\mu$m. Therefore, the generation laser wavelength can be tuned to an optimal wavelength $\lambda_0$ corresponding to an optimal optical penetration depth $\mu_0$. The optimal optical penetration depth $\mu_0$ can generate the desired frequency content in the laser-generated ultrasonic wave. Reference is made to the laser generation system with tunable wavelength disclosed in U.S. patent application Ser. No. 09/361,768, filed on Jul. 27, 1999 to Lorraine, et al., entitled "System And Method For Ultrasonic Laser Testing Using A Laser Source To Generate Ultrasound Having A Tunable Wavelength," hereafter "LORRAINE."

Figure 5:
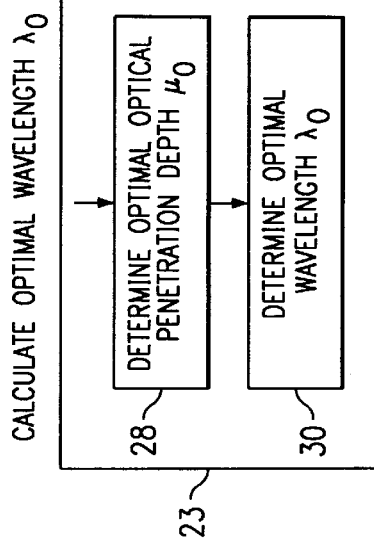
FIG. 5 represents a more detailed flow diagram of step 23 in FIG. 2.

FIG. 5 represents a more detailed representation of step 23 in FIG. 2. At step 28, the optimal optical penetration depth $\mu_0$ is determined using a computer from empirical, material-specific frequency data. A database or storage device accessible to the computer may store the empirical, material-specific frequency data. The empirical, material-specific wavelength data can be of the type illustrated in FIG. 3. At step 30, the optimal wavelength $\lambda_0$ that will produce the optimal optical penetration depth $\mu_0$ (determined at step 28), is determined from empirical, material-specific wavelength data. The empirical, material-specific wavelength data can be stored in a storage device on or accessible to a computer and can be of the type illustrated in FIG. 4.

Figure 6A:
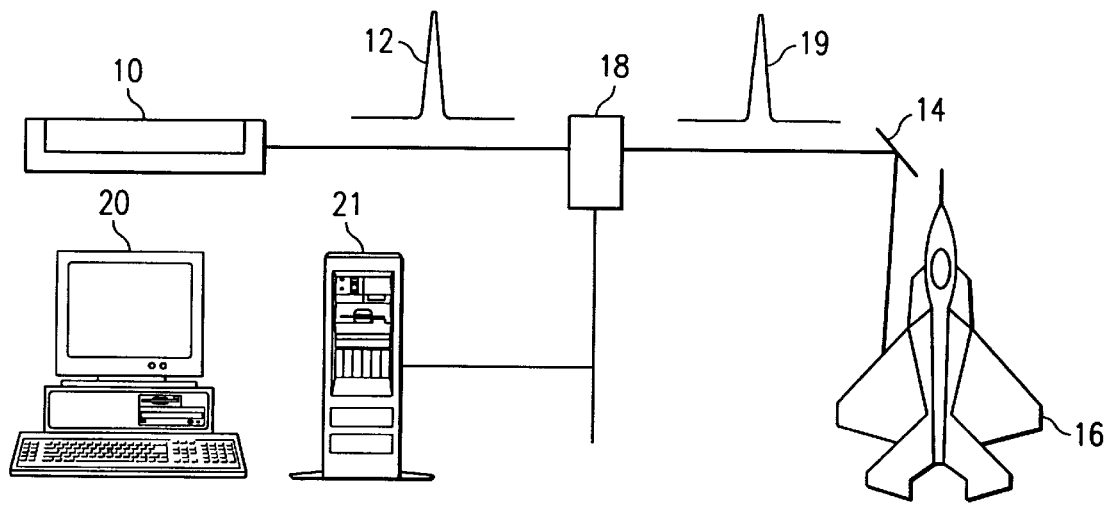
FIGS. 6A and 6B are system block diagrams illustrating one embodiment of the present invention.
Figure 6B:
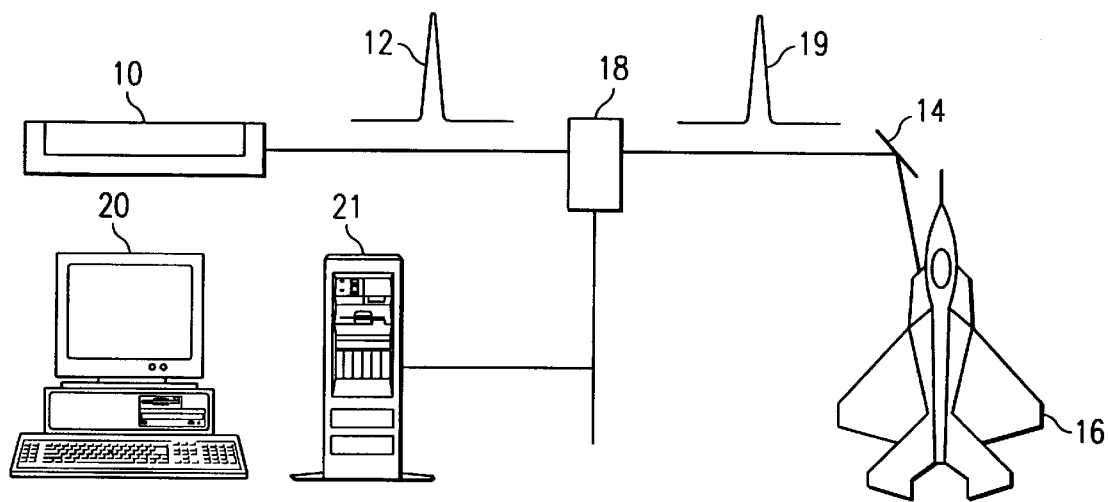

FIGS. 6A and 6B illustrate one embodiment of the present invention employing an optical parametric oscillator (OPO) 18 to shift the wavelength of the laser generation pulse to generate optimal laser pulses for two different regions of a target, such as aircraft 16. The example illustrated in FIGS. 6A and 6B include OPO 18, but any apparatus for tuning the wavelength of generation laser pulse 12 can be used. In FIG. 6A, pulsed laser or tunable pulse laser 10 emits generation pulse 12. Generation pulse 12 is shifted using OPO 18 in conjunction with computer 20 and database 21 to produce optimal laser pulse 19 for inspecting aircraft 16, an optical parametric oscillator, a Raman cell, a Brillouin cell, a difference frequency mixing setup, a sum frequency mixing setup, a harmonic generation setup, the wavelength tuning of the said pulse laser source, or other wavelength shifting device as known to those skilled in the art. Scanning mirror 14 can direct optimal laser pulse 19 to inspect aircraft 16. Various lenses for focusing may also be employed.

The need for shifting generation laser pulse 12 to different wavelengths might arise from different polymers in the composite or different thickness in different regions of aircraft 16. Therefore, computer 20 can determine the optimal optical wavelength $\lambda_0$ from stored empirically calculated, material-specific data. This data can be stored in a storage device, such as database 21. Database 21 can contain data of the type illustrated in FIGS. 3 and 4 for various materials and thicknesses.

FIG. 6B represents the same system as in FIG. 6A, yet generation laser pulse 12 is shifted to a different optimal wavelength $\lambda_O$ for inspection of an alternate region of aircraft 16 optimal for that region. The alternate region may be composed of a different material or have a different thickness. Pulsed laser or tunable pulse laser 10 may be a $CO_2$ laser, Nd:YAG laser, alexandrite laser, titanium sapphire laser or any other laser suitable to wavelength shifting.

This embodiment may be combined with the techniques described in LORRAINE to provide control of the acoustic frequency content by either optical wavelength control or temporal modulation. A further extension is the combination of optical wavelength shifting spatial modulation or patterning of the laser source.

The present invention provides an important technical advantage in that a laser-generated ultrasonic wave can be generated with a desired frequency content. Thus, for certain materials that require a specific frequency range to adequately inspect the material, an optimal penetration depth $\mu_O$ can be determined. Based on the optimal penetration depth $\mu_O$, an optimal wavelength $\lambda_O$ for optimal laser pulse 19 can be determined. OPO 18 can shift generation laser pulse 12 to the optimal wavelength $\lambda_O$ to generate optimal laser pulse 19. Optimal laser pulse 19 generates the desired frequency content in the laser-generated ultrasonic wave. Therefore, depending on the thickness of the material or the material composition, the desired laser-generated ultrasonic wave can be generated and in turn produce increased resolution for target inspection.

Although the present invention has been described in detail herein with reference to the illustrative embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below.

What is claimed is:

1. A method for generating a desired acoustic frequency content in a laser-generated ultrasonic wave emitted from a target in response to a laser pulse, said method comprising:
   implementing a computer to determine an optimal wavelength for said laser pulse, using material-specific, empirically calculated data stored in a storage device;
   generating said laser pulse at a first wavelength using a laser source;
   generating an optimal laser pulse from said laser pulse by shifting said laser pulse to said optimal wavelength; and
   directing said optimal laser pulse to said target to generate said laser-generated ultrasonic wave with said desired frequency content.

2. The method of claim 1, wherein the step of implementing a computer to determine said optimal wavelength further comprises the steps of:
   determining an optimal optical penetration depth from empirically calculated frequency data that produces said laser-generated acoustic wave with a greatest amplitude and said desired frequency content; and
   determining said optimal wavelength that produces said optimal optical penetration depth using empirically calculated wavelength data.

3. The method of claim 2, wherein said empirically calculated frequency data is stored in database accessible to said computer.

4. The method of claim 3, wherein said empirically calculated frequency data comprises individual frequency data for a plurality of materials.

5. The method of claim 2, wherein said empirically calculated wavelength data is stored in a database accessible to said computer.

6. The method of claim 5, wherein said empirically calculated wavelength data comprises individual wavelength data for a plurality of materials.

7. The method of claim 1, wherein said laser source is selected from the group consisting of $CO_2$ laser, Nd:YAG laser, alexandrite laser, or titanium sapphire laser.

8. The method of claim 1, wherein shifting said laser pulse at said first wavelength to said optimal wavelength is completed with a wavelength shifting device selected from a group consisting of an optical parametric oscillator, a Raman cell, a Brillouin cell, a difference frequency mixing setup, a sum frequency mixing setup, and a harmonic generation setup.

9. The method of claim 1, wherein said computer is operable to communicate with a database.

10. The method of claim 1, wherein said target is composed of a composite material.

11. The method of claim 1, wherein said target is composed of multiple types of composite material.

12. A method for generating a desired acoustic frequency content in a laser-generated ultrasonic wave emitted from a target in response to a laser pulse, said method comprising:
   implementing a computer to determine, using empirically calculated frequency data, an optimal optical penetration depth that produces said laser-generated acoustic wave with a greatest amplitude and said desired frequency content;
   implementing said computer to determine, using empirically calculated frequency data, an optimal wavelength that produces said optimal optical penetration depth;
   generating said laser pulse at a first wavelength using a laser source;
   shifting said laser pulse to said optimal wavelength to create an optimal laser pulse; and
   directing said optimal laser pulse to said target to generate said laser-generated ultrasonic wave with said desired frequency content.

13. The method of claim 12, wherein said empirically calculated frequency data is stored in a database accessible to said computer.

14. The method of claim 13, wherein said empirically calculated frequency data comprises individual frequency data for a plurality of materials.

15. The method of claim 12, wherein said empirically calculated wavelength data is stored in a database accessible to said computer.

16. The method of claim 15, wherein said empirically calculated wavelength data comprises individual wavelength data for a plurality of materials.

17. The method of claim 12, wherein said laser source is selected from the group consisting of $CO_2$ laser, Nd:YAG laser, alexandrite laser, or titanium sapphire laser.

18. The method of claim 12, wherein shifting said laser pulse at said first wavelength to said optimal wavelength is completed with an optical parametric oscillator.

19. The method of claim 12, wherein said computer is operable to communicate with a database.

20. The method of claim 12, wherein said target is composed of a composite material.

21. The method of claim 12, wherein said target is composed of multiple types of composite material.

22. A system for generating a desired acoustic frequency content in a laser-generated ultrasonic wave emitted from a target in response to a laser pulse, said system comprising:
  a computer for determining:
    an optimal optical penetration depth that produces said laser-generated acoustic wave with a greatest amplitude and said desired frequency content using empirically calculated frequency data; and
    an optimal wavelength that produces said optimal optical penetration depth using empirically calculated wavelength data;
  a laser source for generating said laser pulse at a first wavelength; and
  a wavelength shifting device for shifting said laser pulse to said optimal wavelength to create an optimal laser pulse used to generate said laser-generated ultrasonic wave with said desired frequency content.

23. The system of claim 22, wherein said empirically calculated frequency data is stored in a database accessible to said computer.

24. The system of claim 23, wherein said empirically calculated frequency data comprises individual frequency data for a plurality of materials.

25. The system of claim 22, wherein said empirically calculated wavelength data is stored in a database accessible to said computer.

26. The system of claim 25, wherein said empirically calculated wavelength data comprises individual wavelength data for a plurality of materials.

27. The system of claim 22, wherein said laser source is selected from the group consisting of $CO_2$ laser, Nd:YAG laser, alexandrite laser, or titanium sapphire laser.

28. The system of claim 22, wherein shifting said laser pulse at said first wavelength to said optimal wavelength is completed with an optical parametric oscillator.

29. The system of claim 22, wherein said computer is operable to communicate with a database.

30. The system of claim 22, wherein said target is composed of a composite material.

31. The system of claim 22, wherein said target is composed of multiple types of composite material.

* * * * *